US012390633B2

(12) United States Patent
Stotz et al.

(10) Patent No.: US 12,390,633 B2
(45) Date of Patent: Aug. 19, 2025

(54) BEARING DEVICE FOR A HEART SUPPORT SYSTEM, AND METHOD FOR RINSING A SPACE IN A BEARING DEVICE FOR A HEART SUPPORT SYSTEM

(71) Applicant: KARDION GMBH, Stuttgart (DE)

(72) Inventors: Ingo Stotz, Ditzingen (DE); Fabian Eiberger, Gerlingen (DE)

(73) Assignee: Kardion GmbH, Stuttgart (DE)

( * ) Notice: Subject to any disclaimer, the term of this patent is extended or adjusted under 35 U.S.C. 154(b) by 1196 days.

(21) Appl. No.: 17/266,044

(22) PCT Filed: Aug. 7, 2019

(86) PCT No.: PCT/EP2019/071233
§ 371 (c)(1),
(2) Date: Sep. 29, 2021

(87) PCT Pub. No.: WO2020/030700
PCT Pub. Date: Feb. 13, 2020

(65) Prior Publication Data
US 2022/0008714 A1   Jan. 13, 2022

(30) Foreign Application Priority Data
Aug. 7, 2018   (DE) .......................... 102018213150.3

(51) Int. Cl.
*A61M 60/824* (2021.01)
*A61M 60/178* (2021.01)
(Continued)

(52) U.S. Cl.
CPC ........ *A61M 60/824* (2021.01); *A61M 60/178* (2021.01); *A61M 60/183* (2021.01);
(Continued)

(58) Field of Classification Search
CPC .. A61M 60/237; A61M 60/82; A61M 60/216; A61M 60/804; A61M 60/806
See application file for complete search history.

(56) References Cited

U.S. PATENT DOCUMENTS

| 2,254,698 A | 9/1941 | Hansen, Jr. |
| 2,310,923 A | 2/1943 | Bean |

(Continued)

FOREIGN PATENT DOCUMENTS

| AU | 7993698 | 2/1999 |
| AU | 2002308409 | 12/2005 |

(Continued)

OTHER PUBLICATIONS

"ABMD—Taking a Closer Look at Impella ECP as the Pivotal Trial Gets Underway", Guggenheim, Press Release, Mar. 29, 2022, pp. 4.
(Continued)

*Primary Examiner* — Christopher D. Prone
(74) *Attorney, Agent, or Firm* — Knobbe Martens Olson & Bear LLP

(57) ABSTRACT

The invention relates to a bearing device (100) for a cardiac support system. The bearing device (100) comprises a stand unit (105) and an impeller (110). The stand unit (105) is designed to support the impeller (110) such that it can rotate. The impeller (110) is designed to rotate during an operation of the cardiac support system in order to convey a pump fluid flow (115). The impeller (110) is designed to enclose at least one subsection (120) of the stand unit (105) in the assembled state of the bearing device (100), wherein an intermediate space (125) for guiding a flushing fluid flow (130) is provided between the subsection (120) and the impeller (110). At least one flushing outlet (135) is formed in the impeller (110). The flushing outlet (135) is designed to discharge the flushing fluid flow (130) from the interme- (Continued)

diate space (125) by means of centrifugal force when the cardiac support system is in operation.

20 Claims, 10 Drawing Sheets

(51) Int. Cl.
    *A61M 60/183*     (2021.01)
    *A61M 60/216*     (2021.01)
    *A61M 60/232*     (2021.01)
    *A61M 60/806*     (2021.01)
    *A61M 60/82*     (2021.01)
    *A61M 60/825*     (2021.01)

(52) U.S. Cl.
    CPC ........ *A61M 60/216* (2021.01); *A61M 60/232* (2021.01); *A61M 60/806* (2021.01); *A61M 60/82* (2021.01); *A61M 60/825* (2021.01)

(56) References Cited

U.S. PATENT DOCUMENTS

| | | |
|---|---|---|
| 3,085,407 A | 4/1963 | Tomlinson |
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,245,622 A | 1/1981 | Hutchins, IV |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,702,430 A | 12/1997 | Larson, Jr. et al. |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,964,694 A | 10/1999 | Siess et al. |
| 6,001,056 A | 12/1999 | Jassawalla et al. |
| 6,007,303 A | 12/1999 | Schmidt |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,579,257 B1 | 6/2003 | Elgas et al. |
| 6,589,031 B2 | 7/2003 | Maeda et al. |
| 6,592,620 B1 | 7/2003 | Lancisi et al. |
| 6,595,743 B1 | 7/2003 | Kazatchkov et al. |
| 6,607,368 B1 | 8/2003 | Ross et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,011,620 B1 | 3/2006 | Siess |
| 7,014,620 B2 | 3/2006 | Kim |
| 7,022,100 B1 | 4/2006 | Aboul-Hosn et al. |
| 7,027,875 B2 | 4/2006 | Siess et al. |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |
| 7,502,648 B2 | 3/2009 | Okubo et al. |
| 7,736,296 B2 | 6/2010 | Siess et al. |
| 7,762,941 B2 | 7/2010 | Jarvik |

(56) References Cited

U.S. PATENT DOCUMENTS

| | | |
|---|---|---|
| 7,798,952 B2 | 9/2010 | Tansley et al. |
| 7,841,976 B2 | 11/2010 | McBride et al. |
| 7,850,593 B2 | 12/2010 | Vincent et al. |
| 7,878,967 B1 | 2/2011 | Khanal |
| 7,914,436 B1 | 3/2011 | Kung |
| 7,934,909 B2 | 5/2011 | Nuesser et al. |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |

(56) References Cited

U.S. PATENT DOCUMENTS

| | | |
|---|---|---|
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,773,002 B2 | 9/2020 | Siess et al. |
| 10,814,053 B2 | 10/2020 | Throckmorton et al. |
| 10,857,273 B2 | 12/2020 | Hodges et al. |
| 10,864,308 B2 | 12/2020 | Muller et al. |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |

(56) References Cited

U.S. PATENT DOCUMENTS

| | | |
|---|---|---|
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,551 B2 | 10/2023 | Yanai et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,443 B2 | 11/2023 | Hanson et al. |
| 11,813,444 B2 | 11/2023 | Siess et al. |
| 11,819,678 B2 | 11/2023 | Siess et al. |
| 11,826,127 B2 | 11/2023 | Casas |
| 11,833,278 B2 | 12/2023 | Siess et al. |
| 11,833,342 B2 | 12/2023 | Tanner et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| 11,857,743 B2 | 1/2024 | Fantuzzi et al. |
| 11,857,777 B2 | 1/2024 | Earles et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| 11,890,212 B2 | 2/2024 | Gilmartin et al. |
| 11,896,482 B2 | 2/2024 | Delaloye et al. |
| 11,898,642 B2 | 2/2024 | Stanton et al. |
| 11,904,104 B2 | 2/2024 | Jahangir |
| 11,911,579 B2 | 2/2024 | Tanner et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,938,311 B2 | 3/2024 | Corbett et al. |
| 11,944,805 B2 | 4/2024 | Stotz |
| 11,980,385 B2 | 5/2024 | Haselman |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,023,476 B2 | 7/2024 | Tuval et al. |
| 12,023,477 B2 | 7/2024 | Siess |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| 12,076,544 B2 | 9/2024 | Siess et al. |
| 12,076,549 B2 | 9/2024 | Stotz et al. |
| 12,090,314 B2 | 9/2024 | Tuval et al. |
| 12,092,114 B2 | 9/2024 | Siess |
| 12,097,016 B2 | 9/2024 | Goldvasser |
| 12,107,474 B2 | 10/2024 | Vollmer |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0147495 A1 | 10/2002 | Petroff |
| 2002/0153664 A1 | 10/2002 | Schroeder |
| 2003/0060685 A1 | 3/2003 | Houser |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |
| 2004/0044266 A1 | 3/2004 | Siess et al. |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2005/0254976 A1 | 11/2005 | Carrier et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2008/0306328 A1 | 12/2008 | Ercolani |
| 2009/0004037 A1 | 1/2009 | Ito |
| 2009/0112312 A1 | 4/2009 | Larose et al. |
| 2009/0138080 A1 | 5/2009 | Siess et al. |
| 2009/0203957 A1 | 8/2009 | LaRose et al. |
| 2009/0204205 A1 | 8/2009 | Larose et al. |

(56) References Cited

U.S. PATENT DOCUMENTS

| | | |
|---|---|---|
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0268017 A1 | 10/2010 | Siess |
| 2010/0298625 A1 | 11/2010 | Reichenbach et al. |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0029265 A1 | 2/2012 | LaRose |
| 2012/0035645 A1 | 2/2012 | Gross |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141842 A1 | 5/2015 | Spanier et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0144089 A1 | 5/2016 | Woo et al. |
| 2016/0144166 A1 | 5/2016 | Decréet al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0256620 A1 | 9/2016 | Scheckel et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0043074 A1 | 2/2017 | Siess |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-Hardt et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0232169 A1 | 8/2017 | Muller |
| 2017/0271971 A1 | 9/2017 | Riemay et al. |
| 2017/0274128 A1 | 9/2017 | Tamburino et al. |
| 2017/0317573 A1 | 11/2017 | Mueller et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1* | 8/2018 | Siess ................. A61M 60/857 |
| 2018/0243004 A1 | 8/2018 | Von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311421 A1* | 11/2018 | Tuseth ................. A61M 60/17 |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |

(56) References Cited

U.S. PATENT DOCUMENTS

| | | |
|---|---|---|
| 2019/0211847 A1 | 7/2019 | Walsh et al. |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0261633 A1 | 8/2020 | Spanier |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0384812 A1 | 12/2021 | Vollmer et al. |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0323742 A1 | 10/2022 | Grauwinkel et al. |
| 2022/0407403 A1 | 12/2022 | Vogt et al. |
| 2023/0001178 A1 | 1/2023 | Corbett et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0075277 A1 | 3/2024 | Schellenberg |
| 2024/0102475 A1 | 3/2024 | Schuelke et al. |
| 2024/0198084 A1 | 6/2024 | Stotz |
| 2024/0245902 A1 | 7/2024 | Schlebusch et al. |
| 2024/0269459 A1 | 8/2024 | Schellenberg et al. |
| 2024/0277998 A1 | 8/2024 | Vogt et al. |
| 2024/0285935 A1 | 8/2024 | Popov et al. |
| 2024/0335651 A1 | 10/2024 | Mitze et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 292 432 | 5/1998 |
| CA | 2 664 835 | 2/2008 |
| CA | 2 796 357 | 10/2011 |
| CA | 2 947 984 | 11/2022 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 101128168 | 2/2008 |
| CN | 201150675 | 11/2008 |
| CN | 101677812 | 3/2010 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |

(56) References Cited

FOREIGN PATENT DOCUMENTS

| | | |
|---|---|---|
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 27 07 951 | 9/1977 |
| DE | 26 24 058 | 12/1977 |
| DE | 3 545 214 | 7/1986 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 039 658 | 3/2011 |
| DE | 20 2009 018 416 | 8/2011 |
| DE | 10 2010 041 995 | 4/2012 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 119 451 | 6/2019 |
| EP | 3 536 360 | 9/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 740 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |

(56) References Cited

FOREIGN PATENT DOCUMENTS

| | | |
|---|---|---|
| EP | 3 556 409 | 1/2022 |
| EP | 3 624 868 | 1/2022 |
| EP | 3 930 785 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 2 961 984 | 9/2023 |
| EP | 3 352 808 | 9/2023 |
| EP | 3 554 576 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 3 854 444 | 9/2024 |
| FR | 1458525 | 3/1966 |
| FR | 2 768 056 | 3/1999 |
| GB | 0 648 739 | 1/1951 |
| GB | 2 213 541 | 8/1989 |
| GB | 2 335 242 | 9/1999 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515374 | 9/2001 |
| JP | 2001-515375 | 9/2001 |
| JP | 2003-019197 | 1/2003 |
| JP | 2003-525438 | 8/2003 |
| JP | 2004-019468 | 1/2004 |
| JP | 2004-278375 | 10/2004 |
| JP | 2005-028137 | 2/2005 |
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 | 1/2017 |
| JP | 6267625 | 1/2018 |
| JP | 2018-057878 | 4/2018 |
| JP | 6572056 | 9/2019 |
| JP | 2020-072985 | 5/2020 |
| JP | 2018-510708 | 3/2021 |
| KR | 10-2011-0098192 | 9/2011 |

(56) References Cited

FOREIGN PATENT DOCUMENTS

| | | |
|---|---|---|
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO-2008017289 A2 * | 2/2008 ............ A61M 1/101 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/036927 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |
| WO | WO 2023/230157 | 11/2023 |

OTHER PUBLICATIONS

Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.

(56) References Cited

OTHER PUBLICATIONS

International Search Report and Written Opinion received in PCT Application No. PCT/EP2019/071233, dated Sep. 6, 2019 in 11 pages.
International Preliminary Report on Patentability and Written Opinion received in PCT Application No. PCT/EP2019/071233, dated Feb. 18, 2021 in 14 pages.
"Edwards SAPIEN 3 Kit—Transapical and Transaortic", Edwards Lifesciences, Released Nov. 8, 2016, pp. 11. chrome-extension:// efaidnbmnnnibpcajpcglclefindmkaj/https://edwardsprod.blob.core. windows.net/media/De/sapien3/doc-0045537b%20-%20certitude. pdf.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
Gopinath, Divya, "A System for Impedance Characterization of Coronary Stents", University of Strathclyde Engineering, Thesis, Aug. 2015, pp. 77.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
Neale, Michael J., "The Tribology Handbook;" 1999, Butterworth-Heinemann, Second Edition, pp. 582.
Park et al., "A Novel Electrical Potential Sensing Method for in Vitro Stent Fracture Monitoring and Detection", Jan. 1, 2011, vol. 21, No. 4, pp. 213-222.
Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.

\* cited by examiner

BEARING DEVICE FOR A HEART SUPPORT SYSTEM, AND METHOD FOR RINSING A SPACE IN A BEARING DEVICE FOR A HEART SUPPORT SYSTEM

BACKGROUND

Field

The invention relates to a bearing device for a cardiac support system comprising a stand unit, an impeller and an intermediate space formed between the impeller and the stand unit for guiding a flushing fluid flow of a fluid, wherein the stand unit comprises a subsection which projects into the impeller and is configured to support the impeller such that it can rotate about an axis of rotation, wherein the impeller is configured to rotate about a longitudinal axis aligned with the axis of rotation when the cardiac support system is in operation to convey a pump fluid flow of the fluid in a flow direction, and wherein the impeller comprises at least one flushing inlet for introducing the flushing fluid flow into the intermediate space and at least one flushing outlet for discharging the flushing fluid flow from the intermediate space.

The invention further relates to a cardiac support system having a bearing device and a method for flushing an intermediate space for guiding a flushing fluid flow with a fluid in a bearing device for a cardiac support system and a method for producing a bearing device for a cardiac support system.

Description of the Related Art

To provide cardiovascular support for patients having heart failure, systems are used in particular that take over part or all of the heart's pumping function. These systems, which are also referred to as cardiac support systems or VADs (ventricular assist devices) for short, can be subdivided into temporary systems for short-term cardiac support and permanent systems for long-term use on or in the patient. One component of such a system is usually a blood pump, typically a centrifugal pump (turbo pump), which is driven by an integrated electric motor and produces the required blood flow by means of a rotor. The pump can be implanted in different locations. The pump can be sutured to the heart from the outside by means of an invasive sternotomy, for example, or it can be placed into the aorta or into a ventricle in a minimally invasive manner by means of a catheter. In the latter case, the maximum permissible outer diameter of the pump is generally limited to 10 mm, which is why the use of an axial pump having a rotor which receives flow axially is desirable. In the process, the blood to be conveyed is expelled through the discharge openings disposed on the circumference of a cylindrical pump housing in order to be returned to the aorta.

EP 3 127 562 A1 discloses a blood pump for a cardiac support system, which comprises a pump housing with an impeller that is rotatably mounted in the pump housing in a sliding bearing having stationary support surfaces, against which support surfaces configured on the blades of the impeller abut. The complex structure of the blades of the impeller on which the support surfaces are formed has the effect that the sliding bearing is flushed and heat is removed from it when blood is pumped in the blood pump.

SUMMARY

The object of the invention is to provide a bearing device for a cardiac support system that does not require complex blade structures and/or hoses with additional flushing pumps for flushing with a fluid, and to specify a method for flushing a bearing device for a cardiac support system that ensures that sufficient heat can be dissipated from the bearing device during operation of the cardiac support system.

This object is achieved by the bearing device specified herein and the method specified herein. Advantageous embodiments of the invention are described herein.

A bearing device according to the invention for a cardiac support system includes a stand unit and an impeller and comprises an intermediate space formed between the impeller and the stand unit for guiding a flushing fluid flow of a fluid. The stand unit comprises a subsection which projects into the impeller and is configured to support the impeller such that it can rotate about an axis of rotation. The impeller is configured to rotate about a longitudinal axis aligned with the axis of rotation when the cardiac support system is in operation to convey a pump fluid flow of the fluid in a flow direction, wherein the impeller comprises at least one flushing outlet for discharging the flushing fluid flow from the intermediate space. The at least one flushing outlet in the impeller is configured such that, due to a centrifugal force acting upon the fluid in the at least one flushing outlet, a rotation of the impeller about the axis of rotation during operation of the cardiac support system causes the fluid to be expelled from the intermediate space through the flushing outlet to at least one discharge opening, whereby the flushing fluid flow is discharged from the intermediate space. For this purpose, the at least one flushing outlet in the impeller can comprise a discharge opening for discharging the flushing fluid flow, which has an opening cross-section, in which, at at least one location, an opening cross-section normal vector has a directional component which faces away from the axis of rotation and is radial to the axis of rotation. The at least one flushing outlet in the impeller is configured such that, due to a centrifugal force acting upon the fluid in the at least one flushing outlet, a rotation of the impeller about the axis of rotation during operation of the cardiac support system causes the fluid to be expelled from the intermediate space through the flushing outlet to at least one discharge opening, whereby the flushing fluid flow is discharged from the intermediate space.

A plurality of flushing outlets can be formed in the impeller. The at least one flushing outlet preferably extends along an axis which intersects the longitudinal axis of the impeller or is disposed at an angle to said longitudinal axis. The at least one flushing outlet can in particular be configured as a tube. The at least one discharge opening of the flushing outlet can, for example, be disposed in a jacket section of the impeller enclosing the subsection of the stand unit projecting into the impeller. The at least one discharge opening of the flushing outlet can in particular be disposed in a transition section between a region of a propeller of the impeller and a jacket section of the impeller enclosing the subsection of the stand unit projecting into the impeller.

It is also possible for the impeller to comprise a plurality of flushing outlets, wherein the at least one discharge openings of the flushing outlet are disposed at least partially in a transition section between a region of a propeller of the impeller and a jacket section of the impeller enclosing the subsection of the stand unit projecting into the impeller.

It should be noted that a number of flushing outlets in the impeller can correspond to a multiple of the number of blades of the impeller. It should also be noted that the bearing device can have a flushing inlet which, in the assembled state of the sliding bearing device, opens into the intermediate space. The flushing inlet can be configured as a gap between a base of the stand unit and a jacket section of the impeller enclosing the subsection of the stand unit projecting into the impeller, for example.

It should be noted that the flushing inlet can also be configured as at least one inlet channel extending in a direction which intersects the longitudinal axis of the impeller or extends at an angle to said longitudinal axis. The bearing device can also comprise a flushing inlet having a plurality of inlet channels.

The flushing inlet can in particular be disposed downstream with respect to the flushing outlet in the flow direction of the pump fluid flow.

The impeller can be located in a housing comprising a housing section to which an inlet hose for supplying the fluid is connected.

The housing section of the bearing device preferably has at least one discharge opening for discharging the pump fluid flow. The housing section can comprise webs for connecting to a connection section for connecting an inlet hose, wherein the webs delimit at least one discharge opening of the housing section.

A bearing device according to the invention can be configured as a sliding bearing device which comprises a sliding bearing for supporting a rotating component, or as a magnetic bearing device, in which a rotating component is magnetically supported.

A sliding bearing device according to the invention comprises a stand unit and an impeller. The stand unit is designed to support the impeller such that it can rotate. The impeller is designed to rotate during an operation of the cardiac support system in order to convey a pump fluid flow. The impeller is configured to enclose at least one subsection of the stand unit in the assembled state of the sliding bearing device. An intermediate space for guiding a flushing fluid flow is provided between said subsection and the impeller. At least one flushing outlet is configured in the impeller to discharge the flushing fluid flow from the intermediate space by means of centrifugal force when the cardiac support system is in operation.

A sliding bearing device according to the invention for a cardiac support system in particular enables the sliding bearing device to be flushed by utilizing centrifugal force. For this purpose, an impeller of the sliding bearing device can comprise a flushing outlet that rotates with the impeller in order to use the centrifugal force at the rotating flushing outlet as the driving force for flushing the sliding bearing device. Flushing the sliding bearing device is beneficial during operation of the cardiac support system to dissipate heat and prevent the formation of thromboses.

Flushing that utilizes centrifugal force, as a result of which the flushing rate substantially depends only on the rotational speed of the cardiac support system and not on the static pressure difference between the flushing inlet and the flushing outlet, advantageously reduces the risk of thrombosis formation, because the flushing rate is significantly less affected by loss of pressure in the blood stream and can thus be set more robustly. It is also not necessary for an external pressure difference to be imposed via the flushing system.

The utilization of the centrifugal force via the flushing outlet in the impeller furthermore enables a compact design of the sliding bearing device, which is advantageous in particular for the use of the sliding bearing device in conjunction with the cardiac support system.

The cardiac support system can be a heart pump, for example, such as a left ventricular support system, a right ventricular support system, or a biventricular support system. The stand unit can be understood to be a non-rotating component of the sliding bearing device. The impeller can be a rotating component, such as a rotor. In the assembled state of the sliding bearing device, the impeller can enclose at least one subsection of the stand unit, whereby the sliding bearing device can be configured as a cylindrical sliding bearing, for example. In the implanted state of the cardiac support system, the impeller can be positioned in the blood. The pump fluid flow to be conveyed can, for example, be a blood flow pumped by the cardiac support system and produced by means of the cardiac support system. In the assembled state, an intermediate space in the form of a gap can emerge between the impeller and the subsection of the stand unit. The flushing outlet can be realized as a bore or another type of through-opening in the impeller. The flushing outlet can be configured to conduct the flushing fluid flow from the intermediate space through a portion of the impeller to discharge the flushing fluid flow from the intermediate space. It is also possible to configure two or more flushing outlets in the impeller.

According to one embodiment, the flushing outlet can be inclined relative to a longitudinal axis of the impeller, which in particular corresponds to an axis of rotation of the impeller. This is advantageous for utilizing the centrifugal force to effect a flushing of the sliding bearing device. The flushing outlet can have a longitudinal extension axis which is inclined relative to the longitudinal axis of the impeller. The longitudinal extension axis of the flushing outlet can also be inclined at a right angle with respect to the longitudinal axis of the impeller.

According to one embodiment, the flushing outlet can be configured as a tube having a discharge opening. The flushing outlet can thus advantageously be realized in a cost-saving manner, for example as a bore in the impeller, which also enables a compact design of the sliding bearing device.

According to one embodiment, the discharge opening can be disposed in a jacket section of the impeller enclosing the subsection of the stand unit or in a transition section between a region of a propeller of the impeller and said subsection. The transition section can be configured as a narrowing of the jacket section in the direction of the propeller, for example.

The discharge opening can alternatively also be disposed in the region of the propeller. The potential of the centrifugal force, by means of which the flushing effect for flushing the sliding bearing device can advantageously be set, can be set via the positioning of the discharge opening.

According to one embodiment, the impeller can also comprise a plurality of flushing outlets. The discharge openings of the flushing outlets can be disposed at least partially in the transition section. In the assembled state of the sliding bearing device, the flushing outlets can extend radially outward with respect to the stand unit, for example. The discharge openings can be disposed evenly spaced around the periphery of the transition section. This positioning of the flushing outlets and the discharge openings is advantageous in terms of uniform flushing of the intermediate space and in terms of presenting the largest possible cross-section of the flushing outlets.

According to one embodiment, at least one pair of flushing outlets can be configured in the impeller. The flushing outlets of the at least one pair can be disposed opposite one another with respect to a longitudinal axis of the impeller. The configuration of the oppositely disposed pair of flushing outlets is advantageous to prevent an imbalance of the rotating propeller.

A number of flushing outlets in the impeller can correspond to a multiple of the number of blades of the impeller. The flushing outlets in the form of flushing bores are disposed just as periodically as the blading of the impeller, for example. This makes it possible to prevent an imbalance. In this case, for example, two blades result in a multiple of two as the number of flushing outlets.

According to one embodiment, the sliding bearing device can also comprise a flushing inlet for introducing the flushing fluid flow. In the assembled state of the sliding bearing device, the flushing inlet can open into the intermediate space. Using the acting centrifugal force, the flushing fluid flow can flush the intermediate space and thus also the bearing of the sliding bearing device, even without the provision of a static pressure difference between the flushing inlet and the flushing outlet.

According to one embodiment, the flushing inlet can also be configured as a gap between a base of the stand unit and a jacket section of the impeller enclosing the subsection of the stand unit. Additionally or alternatively, the flushing inlet can be configured as an inlet channel in the impeller. The inlet channel can be inclined relative to an axis of rotation of the impeller. The flushing outlet can furthermore be formed in the impeller by a plurality of inlet channels with at least one inclined inlet channel. At least one side of the flushing inlet can thus be configured to be stationary and one side such that it can rotate. The flushing fluid flow can be drawn in on the stationary side of the flushing inlet, e.g., on a wall of the stand unit. If the flushing inlet is configured as an inlet channel in the impeller, the flushing inlet can be configured at least partially in the rotating body of the impeller. A portion of the flushing fluid flow that is partially enclosed in the intermediate space can be introduced through the flushing inlet and discharged again through the flushing outlet, for example to absorb and dissipate heat from the stand unit. The centrifugal pressure is advantageously increased if the flushing inlet is not or only partially located in the rotating body, the impeller.

The flushing inlet can furthermore be disposed downstream with respect to the flushing outlet in the flow direction of the pump fluid flow. By introducing the flushing fluid flow along the stand unit and along the impeller, a constant flushing of the sliding device can advantageously be set thanks to the rotation of the flushing fluid flow at the flushing outlet, even when the pressure levels at the flushing inlet and flushing outlet are the same.

The invention further presents a cardiac support system having an embodiment of the aforementioned sliding bearing device. The cardiac support system can be a left ventricular cardiac support pump, for example. For minimally invasive transfemoral or transaortic insertion, for example, the cardiac support system can furthermore have an elongated, cylindrical shape.

A method for producing a bearing device for a cardiac support system configured as a sliding bearing device or as a magnetic bearing device is presented as well. The method comprises the following steps:

- providing a stand unit, which is designed to support an impeller such that it can rotate, and the impeller, which is configured to rotate during operation of the cardiac support system to convey a pump fluid flow;
- forming at least one flushing outlet in the impeller, wherein the flushing outlet is designed to discharge a flushing fluid flow from the bearing device by means of centrifugal force when the cardiac support system is in operation; and
- assembling the impeller and the stand unit to produce the bearing device, wherein at least one subsection of the stand unit is enclosed by the impeller, and wherein an intermediate space for guiding the flushing fluid flow is disposed between the subsection and the impeller.

An embodiment of the aforementioned bearing device can advantageously be produced by carrying out the method.

The condition for the flushing to function by the action of centrifugal force is set out in the following:

The flushing is independent of the static pressure difference. Centrifugal force is used to flush the sliding bearing device; no external pump or additional geometries or structures to produce a static pressure difference are needed. This requires the mechanical energy balance due to the kinetic rotational energy at the exit, at the discharge opening of the flushing outlet, to be positive; i.e., the mechanical energy of the flow at the exit has to be greater than at the entry, at the flushing inlet. This is illustrated in the following using formulas according to Bernoulli's principle:

$$\frac{p_{exit}}{\text{density}} - \frac{v_{exit}^2}{2} < \frac{p_{entry}}{\text{density}} - \frac{v_{entry}^2}{2}$$

If v is the rotational speed and the flushing inlet is not subject to rotation, then:

$$\frac{p_{exit}}{\text{density}} - \frac{v_{exit}^2}{2} < \frac{p_{entry}}{\text{density}}$$

rearranged:

$$\frac{(p_{exit} - p_{entry})}{\text{density}} < \frac{v_{exit}^2}{2}$$

with the rotation speed $v = 2\pi R n$ and with n being the speed in revolutions/second $$\frac{(p_{exit} - p_{entry})}{\text{density}} < 2(\pi R n)^2$$

from which then follows:

static pressure difference $<< 2(\pi R n)^2 *$ density

For water, the "centrifugal pressure" corresponds to a pressure difference of approx. 5 bar at a radius of 1 cm and a speed of 30,000 revolutions/minute. The described approach is therefore effective for this numerical example if the static pressure difference is only approx. 500 mbar (interpreted as "much greater" than a factor of ten).

Flushing of the sliding bearing device by means of centrifugal force requires a rotating system with system limits, the "entry" and "exit", which point outward in the direction normal to the axis of rotation. The flushing path of the flushing fluid flow extends between the rotating body, the jacket section of the impeller, and the body which is stationary relative to it, the stand unit. According to the design example shown here, the flushing fluid flow moves along the path, i.e., along the intermediate space to the flushing outlet. At the exit of the flushing outlet, the flushing fluid flow flows out of the flushing path. In order to impose the centrifugal force across the entire cross-section, the exit boundary of the flushing outlet is located inside the rotating body, inside the jacket section. The cross-section normal vector should have a component in radial direction, which is not the case on the end face of a cylindrical sliding bearing device, for example, but in radial direction, i.e., when the jacket section is drilled into.

The invention also extends to a cardiac support system in which there is a bearing device as described above.

In a method according to the invention for flushing an intermediate space for guiding a flushing fluid flow with a fluid in a bearing device for a cardiac support system, wherein the intermediate space comprises at least one flushing inlet for introducing the flushing fluid flow and at least one flushing outlet for discharging the flushing fluid flow and wherein the intermediate space is configured between an impeller which can rotate about an axis of rotation for conveying a pump fluid flow and a stand unit for rotatably supporting the impeller, in which the fluid is introduced into the intermediate space through the at least one flushing inlet, the fluid is expelled from the intermediate space through the flushing outlet to at least one discharge opening by means of a centrifugal force acting upon said fluid in the at least one flushing outlet relative to the axis of rotation.

Advantageous design examples of the invention are described in more detail in the following with reference to schematic drawings.

DETAILED DESCRIPTION

In the following description of favorable design examples of the present invention, the same reference signs are used for the elements shown in the various figures, which are the same or have a similar effect, whereby a repeated description of these elements is omitted.

Figure 1:
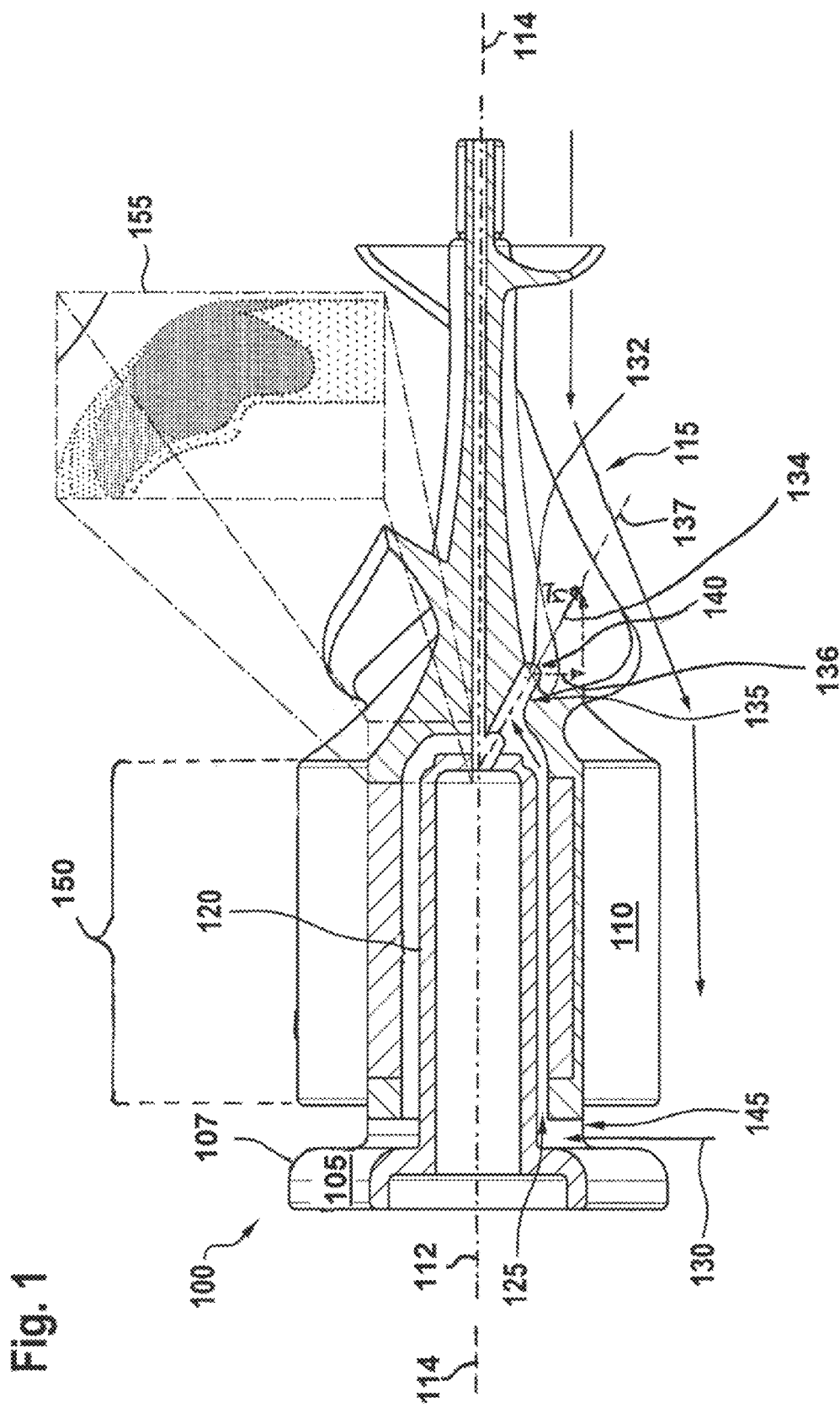
FIG. 1 a first sliding bearing device for a cardiac support system comprising an impeller and comprising a stand unit as a section.

FIG. 1 shows a schematic illustration of a bearing device 100 for a cardiac support system which is configured as a sliding bearing device according to one design example. The bearing device 100 comprises a stand unit 105 and an impeller 110. The stand unit 105 is configured to support the impeller 110 such that it can rotate about an axis of rotation 112 which is coaxial with the longitudinal axis 114 of the impeller 110. The impeller 110 is designed to rotate about the axis of rotation 112 when the cardiac support system is in operation in order to convey a pump fluid flow 115. In the assembled state of the sliding bearing device shown here, the impeller 110 encloses at least one subsection 120 of the stand unit 105. An intermediate space 125 for guiding a flushing fluid flow 130 is provided between the subsection 120 and the impeller 110. At least one flushing outlet 135 is formed in the impeller 110. The flushing outlet 135 is designed to discharge the flushing fluid flow 130 from the intermediate space 125 by means of centrifugal force when the cardiac support system is in operation.

The flushing outlet 135 comprises a discharge opening 140 for discharging the flushing fluid flow 130, which has an opening cross-section 132, in which, at at least one location, an opening cross-section normal vector 134 has a directional component 136 which faces away from the axis of rotation 112 and is radial to the axis of rotation 112.

According to the design example shown here, the flushing outlet 135 is inclined relative to the longitudinal axis 114 of the impeller 110 which is coaxial with the axis of rotation 112. The flushing outlet 135 comprises an axis 137 along which said flushing outlet 135 extends and which is thus a longitudinal extension axis of the flushing outlet 135, which is inclined relative to the longitudinal axis 114 of the impeller 110 and forms an acute angle $\alpha$ with it. It should be noted that this axis 137 can also be inclined relative to the longitudinal axis 114 of the impeller 110.

Furthermore, according to the design example shown here, the flushing outlet 135 is configured as a tube with a discharge opening 140. The discharge opening 140 is disposed at an end of the tube facing away from the intermediate space 125.

According to the design example shown here, the sliding bearing device 100 also comprises a flushing inlet 145 for introducing the flushing fluid flow 130. In the assembled state of the bearing device 100 shown here, the flushing inlet 145 opens into the intermediate space 125.

According to the design example shown here, the flushing inlet 145 is configured as a gap between a base 107 of the stand unit 105 and a jacket section 150 of the impeller 110 enclosing the subsection 120 of the stand unit 105. It should be noted that the flushing inlet can in principle also be configured as an inlet channel in the impeller 110.

In the sliding bearing device shown in FIG. 1, the flushing inlet 145 is disposed downstream with respect to the flushing outlet 135 in the flow direction of the pump fluid flow 115 as in the design example shown here. FIG. 1 shows a flushing fluid flow 130 with a flushing path for flushing the bearing device 100 which extends from the flushing inlet 145 through the intermediate space 125 to the flushing outlet 135 with the discharge opening 140.

Figure 2:
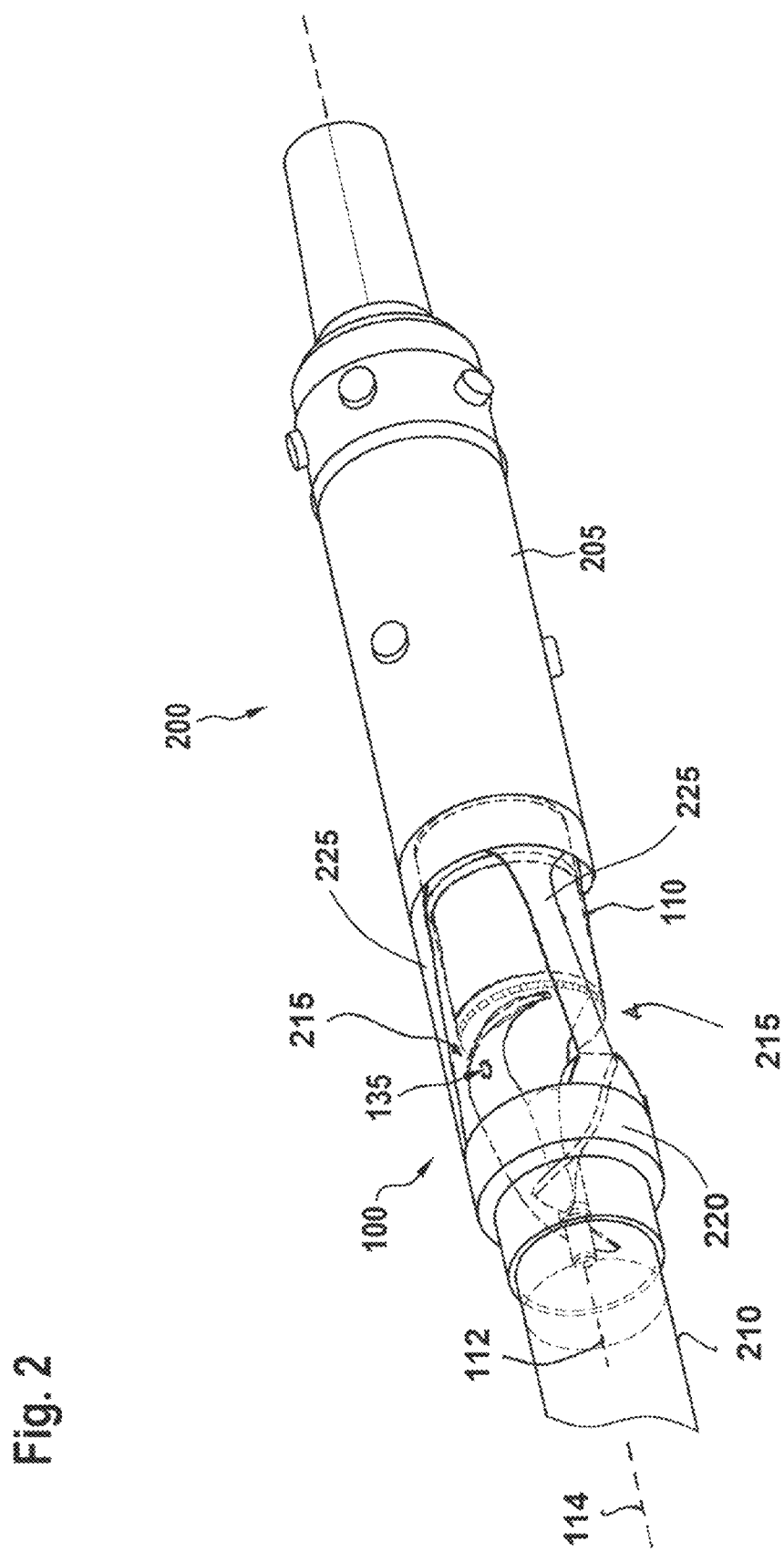
FIG. 2 a portion of a cardiac support system comprising the first sliding bearing device.
Figure 3:
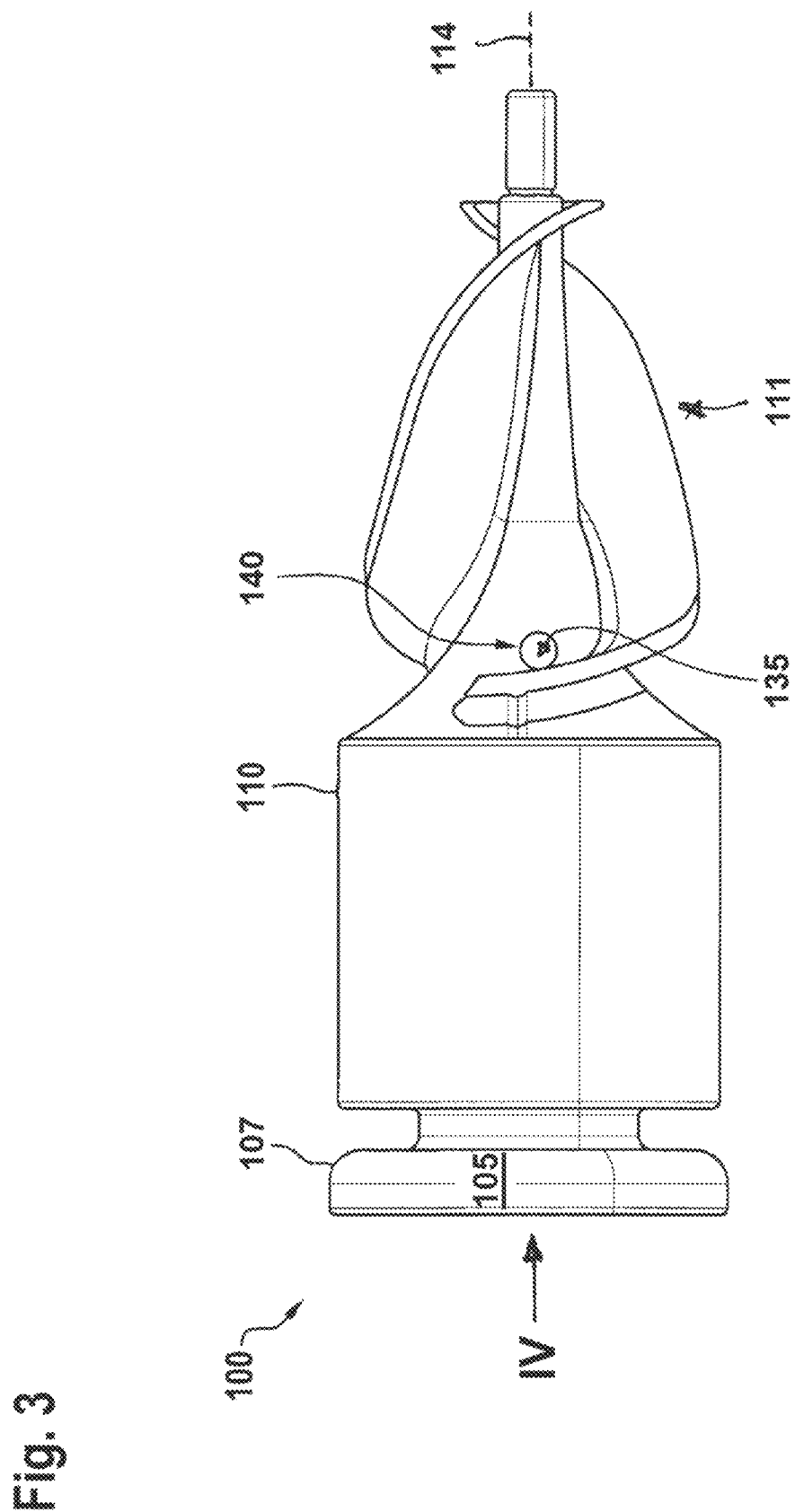
FIG. 3 a side view of the first sliding bearing device.

FIG. 2 shows a perspective view of a portion of a cardiac support system 200 with the sliding bearing device 100 in the form of a left ventricular cardiac support pump (LVAD heart pump). FIG. 3 is a side view of the bearing device 100.

The bearing device 100 and its function in a cardiac support system are described in more detail in the following:

The impeller 110 is a rotor that forms a rotating component in the bearing device 100 of the cardiac support system 200, which is supported magnetically or by means of sliding bearings, wherein the rotating component is positioned over a fluid to dissipate heat or reduce friction. When the impeller 110 is positioned directly in the blood during operation of the cardiac support system, as is the case, for example, with the left ventricular cardiac support pump (LVAD heart pump) shown in FIG. 2 in the implanted state of the cardiac support system, it is beneficial to flush the bearing device 100 to dissipate heat and prevent the formation of thromboses ("blood clotting"). To enable robust flushing of the sliding bearing device 100, a constant flow is necessary. Flushing the sliding bearing device 100 prevents the formation of thromboses. A pump design (such as baffles) that converts mechanical energy into hydrodynamic energy can be used for this purpose. With the sliding bearing device 100 shown in FIG. 1 and FIG. 2, it is possible to utilize the centrifugal force on the flushing outlet 135 rotating with the impeller 110 using only a bore in the form of the flushing outlet 135. The centrifugal force represents the driving force for the flushing. Such a structure is inexpensive to produce.

A plurality of flushing outlets 135 can alternatively also be provided at different locations on the impeller 110 to utilize the centrifugal force, as shown in the following figures.

Using a design example of the bearing device 100 shown here, introduction can be realized by suctioning out the flushing fluid flow 130 with the aid of the centrifugal force at the flushing outlet 135. Structurally, this is achieved by configuring the flushing outlet 135 such that the flushing outlet 135 is enclosed by the rotating component, the impeller 110, e.g., by having a bore as the flushing outlet 135, while the inlet side in the form of flushing inlet 145 is not or only partially, e.g., only on one side, subject to the rotation. This is achieved by configuring the flushing inlet 145 with at least one section of the stand unit 105 as a wall section. In this case, the statistical pressure difference has practically no effect on the flushing flow of the flushing fluid flow 130, which is why the flushing effect of the bearing device 100 is substantially determined by the centrifugal force and the rotational speed of the pump of the cardiac support system. The flushing effect of the bearing device 100 is thus largely independent of other potential influencing variables, such as the magnitude of the mass flow or the level of the pressure build-up through or over the cardiac support system. Consequently, there is no need for a static pressure difference to flush the bearing device 100. The positioning of the flushing outlet 135 in the impeller 110, which is trumpet-shaped here as an example, with widely varying diameters relative to a longitudinal extension axis 114 of said impeller 110, can therefore be realized in different ways, whereby a positioning of the flushing outlet 135 far upstream of the longitudinal extension of the impeller 110 can be omitted. Complex structures, such as a pump wheel, or the application of a pressure difference in or around the sliding bearing device 100 are not necessary to effect the flushing of the sliding bearing device 100 either. Because of the independence from the pump flow, the pump flow of the pump fluid flow 115 shown here, the flushing of the bearing device 100 is possible without an absence of flushing as long as the impeller 110 is rotating.

In the design example discussed here, the bearing device 100 comprises the impeller 110 as a rotating part which, together with the stand unit 105 as a stationary part, forms a cylindrical sliding bearing. The flushing effect of the bearing device 100 is based on the centrifugal force that results from a rotation at the flushing outlet 135. The prerequisite for this is that, as shown here, at least one side at the flushing inlet 145 is stationary; in this case the inner side in the form of the stand unit 105. As a result, even if the pressure levels at the flushing inlet 145 and the flushing outlet 135 are comparable or the same, a constant flushing of the sliding bearing device 100 can be set due to the rotation of both sides of the flushing outlet 135 formed in the rotating impeller 110 or the fluid volume of the flushing outlet 135. The design example of the bearing device 100 shown here also makes it possible to flush a partially enclosed volume, which is shown here in block 155 which, as an example, is disposed around the fixed bearing of the stand unit 105, by combining a rotating and a stationary side. The reason for this is that the flushing fluid flow 130 is accelerated on the rotating side of the impeller as a result of the molecular adhesion conditions. The flushing fluid flow 130 is accelerated along the wall of the intermediate space 125 toward a larger diameter due to the centrifugal force, as a result of which the flushing fluid flow 130 is drawn in on the stationary side of the intermediate space 125 in the form of a wall of the stand unit 105. This causes the partially enclosed fluid of the flushing fluid flow 130 to be flushed, which allows heat at the fixed bearing of the stand unit 105, for example, to be absorbed and dissipated.

The cardiac support system 200 shown in FIG. 2 comprises a housing section 205. The impeller 110 of the bearing device 100 is located in the housing section 205 of the cardiac support system 200. In the cardiac support system 200, the impeller 110 is disposed in a housing section 205 on which an inlet hose 210 for supplying the fluid is provided. In the housing section 205 of the housing of the cardiac support system, there are discharge openings 215 for discharging the pump fluid flow 115. For connecting the inlet hose 210, the cardiac support system 200 comprises a connection section 220 which is connected to webs 225 of the housing section 205 that delimit two discharge openings 215 for discharging fluid conveyed by a rotation of the impeller 110 in the cardiac support system 200 from the housing section 205.

The housing section 205 of the cardiac support system 200 has a cylindrical, elongated structure with a substantially constant outer diameter for easy placement in a blood vessel, such as the aorta, by means of a catheter. The elongated axial design shown here allows transfemoral implantation of the cardiac support system 200. The sliding bearing device 100 is accordingly disposed in a window opening in the housing section 205 such that, in the implanted state of the cardiac support system 200, the rotating rotor component, the impeller 110, is positioned in the blood. Due to the axial design of the cardiac support system 200, the flow received by the impeller 110 is axial relative to the longitudinal axis 114 of the impeller 110, which corresponds to a longitudinal axis of the cardiac support system 200. The flushing outlet 135 in the impeller 110 is disposed in the region 111 of a propeller of the impeller 110, whereby the flushing outlet 135 is realized by a drilled hole or a through-bore or another type of through-hole in the impeller 110.

FIG. 3 shows the sliding bearing device 100 with the stand unit 105 and the impeller 110 in the assembled state, whereby the stand unit 105 forms the non-rotating counterpart to the rotating impeller 110. The stand unit 105 has a section which narrows in the direction of the impeller 110. The narrowed section of the stand unit 105 is mostly enclosed by the impeller 110. The stand unit 105 is connected to the impeller 110 and supports the impeller 110 such that it can rotate. The flushing outlet 135 having a discharge opening 140 is configured in the impeller 105. As an example, the discharge opening 140 of the flushing outlet here is disposed in the region of the propeller of the impeller 110.

Figure 4:
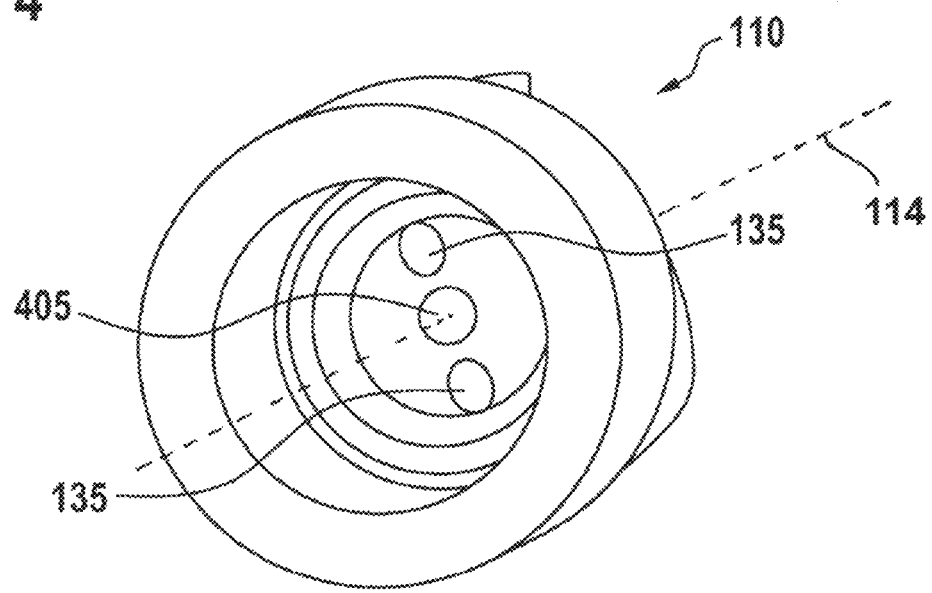
FIG. 4 a rear view of the impeller in the direction of the arrow IV of FIG. 3.

FIG. 4 shows a perspective rear view of the impeller in the direction of the arrow IV of FIG. 3. The side of the impeller 110 facing away from the propeller of the impeller 110, which can be coupled to the stand unit 105 of the bearing device, is shown as the rear side of the impeller 110. To connect the impeller 110 to the stand unit 105, the impeller 110 here comprises a ball bearing 405 for supporting the impeller 110. The flushing outlets 135 of the impeller 110, which, as an example, are configured here as discharge bores and which communicate with the intermediate space 125 shown in FIG. 1, can be seen as well.

According to the design example shown here, at least one pair of flushing outlets 135 is configured in the impeller 110. The flushing outlets 135 of the at least one pair are disposed opposite one another with respect to a longitudinal axis 114 of the impeller 110. As an example, the flushing outlets 135 of the pair are evenly spaced with respect to the axis of rotation 112 of the impeller 110, i.e., they extend symmetrically relative to a longitudinal axis 114 of the impeller 110 coaxial with the axis of rotation 112.

Figure 5:
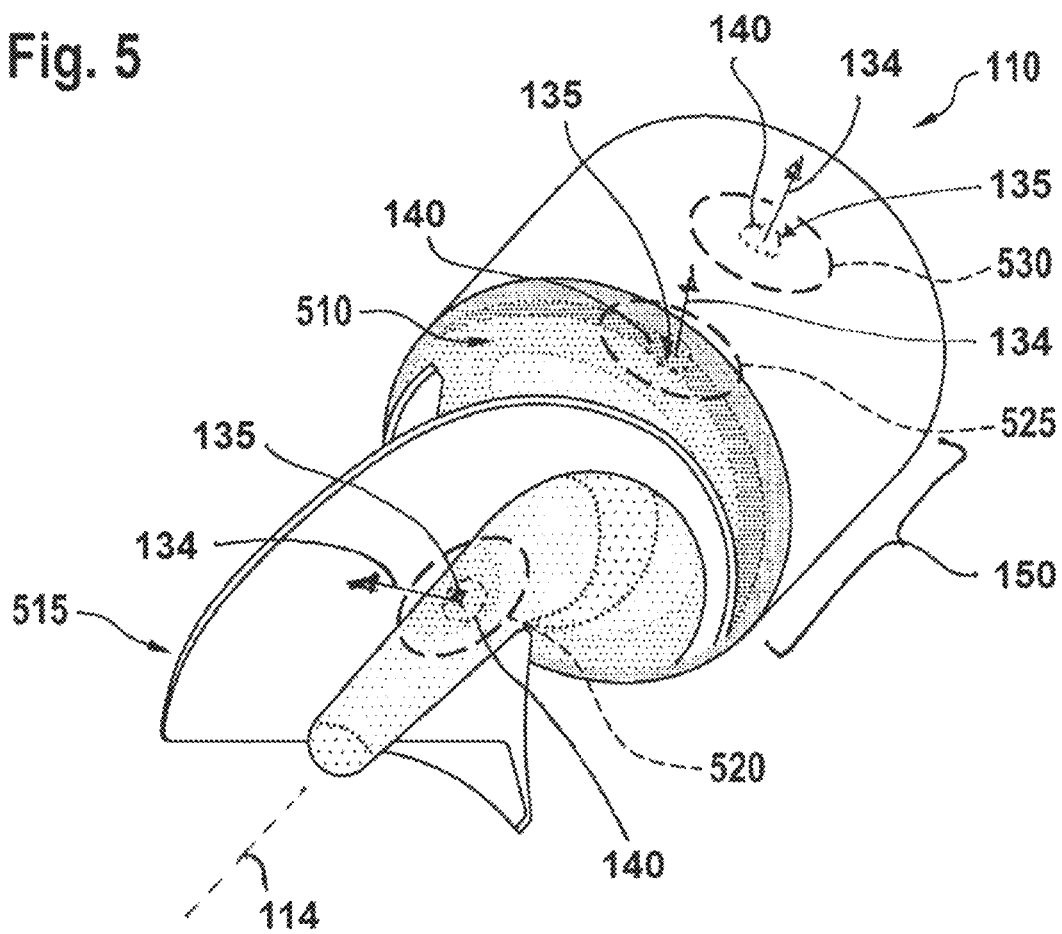
FIG. 5 other possible designs of an impeller in a sliding bearing device for a cardiac support system.

FIG. 5 shows further possible designs of an impeller 110 in a bearing device for a cardiac support system, which can be configured as a sliding bearing device or as a magnetic bearing device. The figure shows a perspective view of the impeller 110, wherein different example positionings of a discharge opening 140 of the flushing outlet 135 in the impeller 110 as well as a respective opening cross-section normal vector 134 and the longitudinal axis 114 of the impeller 110 are identified.

According to one design example, the discharge opening 140 of the flushing outlet 135 is disposed in a jacket section 150 of the impeller 110 enclosing the subsection of the stand unit. Alternatively, the discharge opening of the flushing outlet is disposed in a transition section 510 between a region of a propeller 515 of the impeller 110 and the jacket section 505.

This figure shows a potential estimate for the design example, where the strongest suction force occurs, and thus where a suitable location for positioning the flushing outlet and the discharge opening of the flushing outlet is. Three regions 520, 525 and 530 for disposing the discharge opening of the flushing outlet in the impeller 110 are shown as examples. The region 520 is located in the region of the propeller 515. The region 525, for example, identifies a position of the discharge opening of the flushing outlet 135 in the transition section 510. The region 530, for example, identifies a positioning of the discharge opening of the flushing outlet in the jacket section 150. According to the potential estimate shown here, when the flushing outlet 135 and the discharge opening 140 are positioned in the region 530, a beneficial flushing effect is achieved in a bearing device having such an impeller 110 and a stand unit 105 because the centrifugal force between the flushing inlet and the flushing outlet is sufficient to drive the flushing.

Figure 6:
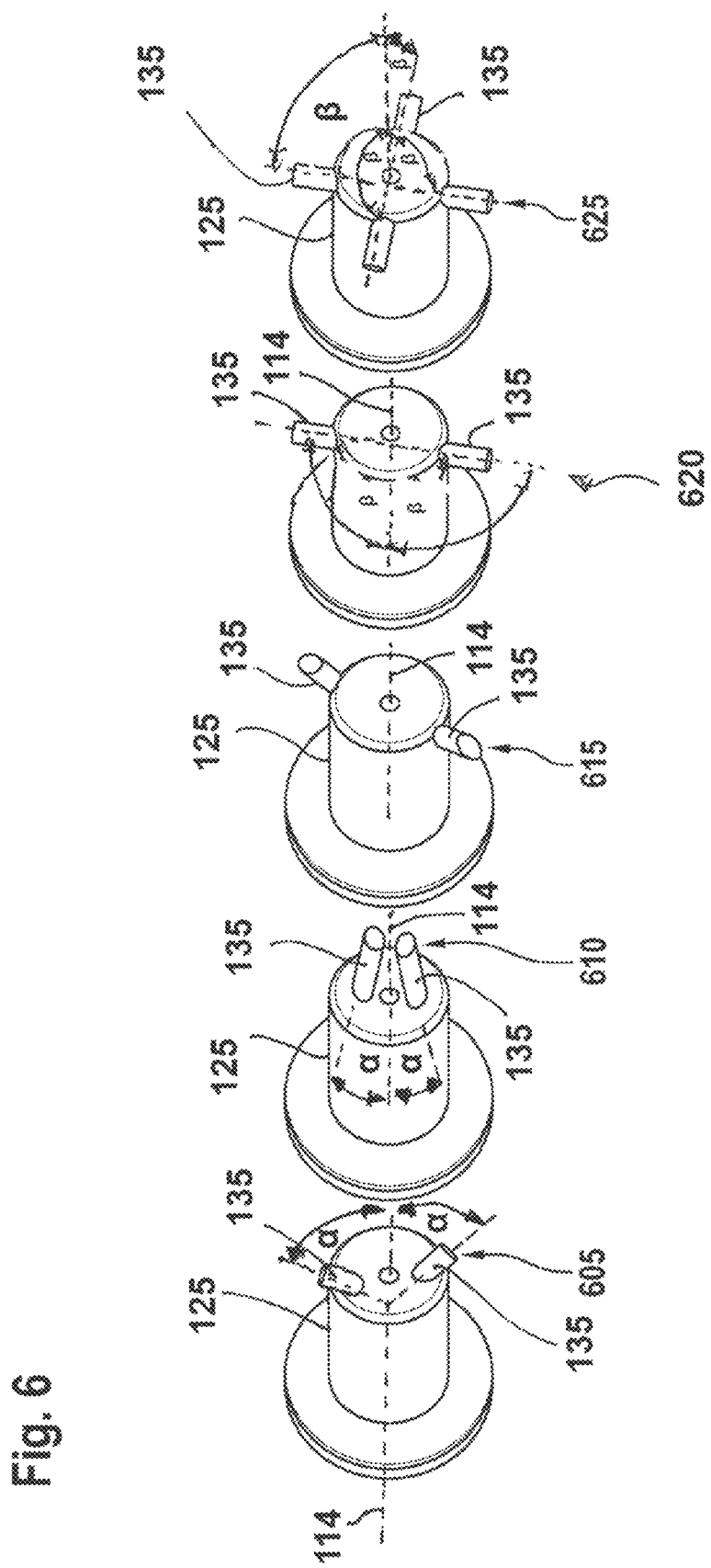
FIG. 6 an intermediate space having various flushing fluid volumes in different sliding bearing devices for a cardiac support system with different configurations of flushing outlets.

FIG. 6 shows the intermediate space 125 with different flushing fluid volumes in different bearing devices for a cardiac support system designed as a sliding bearing device or as a magnetic bearing device having different configurations of flushing outlets, wherein the flushing outlets 135 are configured differently. The flushing outlet 135, through which the flushing fluid flow passes, has different configurations 605, 610, 615, 620, 625 here. At least one pair of flushing outlets 135 is configured in the impeller of these sliding bearing devices, whereby the flushing outlets 135 of the at least one pair in a bearing device are disposed opposite one another with respect to the longitudinal axis 114 of the impeller 110 aligned with the axis of rotation 112. The respective configurations 605, 610, 615, 620, 625 of the flushing outlets shown here show examples of the pair of flushing outlets. In a first configuration 605, the flushing outlets of the pair extend radially from the longitudinal axis 114 of the impeller inclined at an obtuse angle α with respect to said longitudinal axis 114 of the impeller, whereby a starting point of the flushing outlets 135 is formed in close proximity to the longitudinal axis 114. In a second configuration 610, the flushing outlets 135 of the pair extend inclined at an acute angle α with respect to the longitudinal axis 114 of the impeller; the flushing outlets 135 of the pair are accordingly angled toward one another. A third configuration 615 corresponds to the first configuration 605 with the exception of the starting point of the flushing outlets 135, which are disposed further apart than the starting points of the flushing outlets of the first configuration 605. In a fourth configuration 620, the flushing outlets 135 of the pair extend at a right angle β to the longitudinal axis 114 of the impeller. A fifth configuration 625 shows an example of two pairs of flushing outlets 135, which are disposed opposite one another with respect to the longitudinal axis 114 of the impeller and are disposed evenly spaced apart from one another. Like the pair shown in the fourth configuration 620, the two pairs of flushing outlets 135 extend at a right angle β to the longitudinal axis 114 of the impeller.

Figure 7:
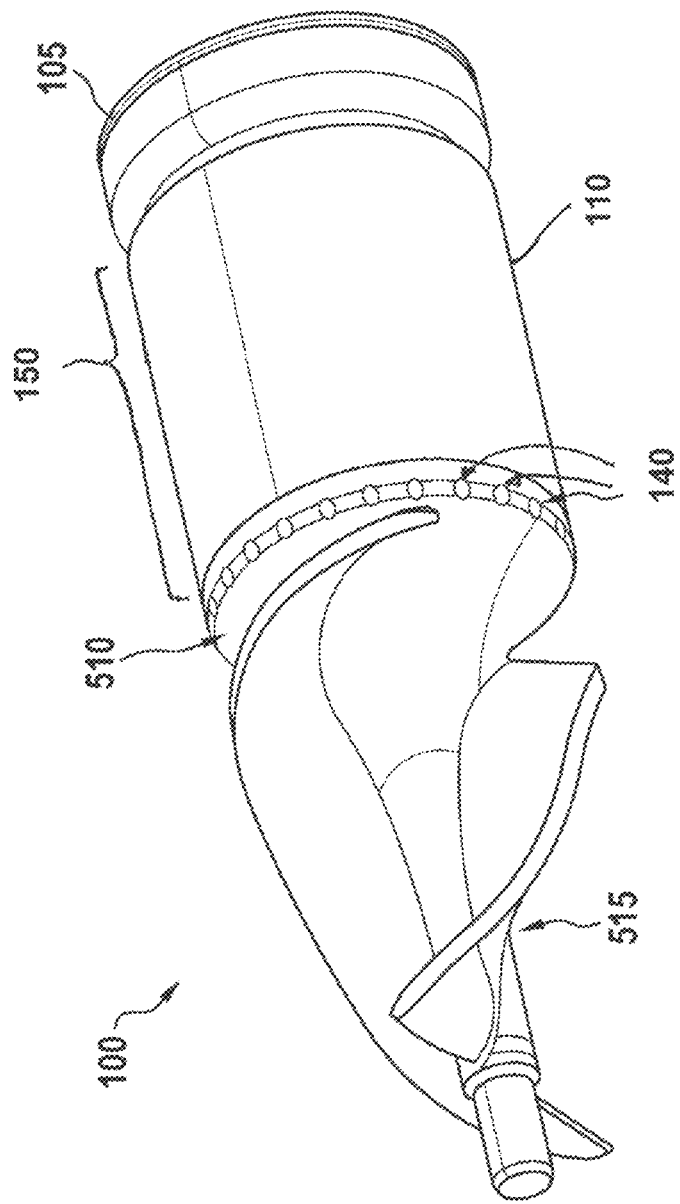
FIG. 7 a further sliding bearing device comprising an impeller and comprising a stand unit.
Figure 8:
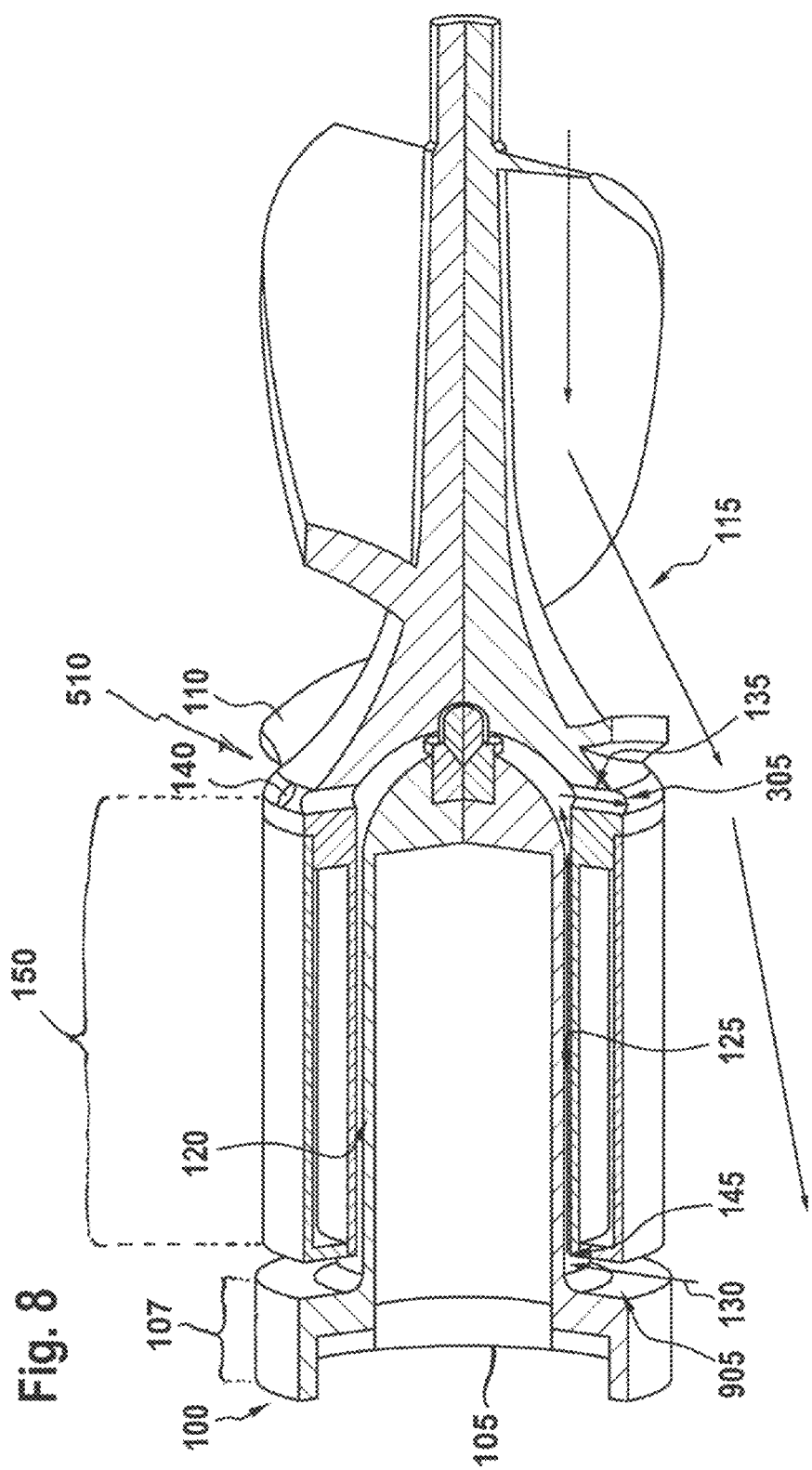
FIG. 8 the further sliding bearing device comprising an impeller and comprising a stand unit as a section.

FIG. 7 shows a further sliding bearing device 100 for a cardiac support system. The figure shows a perspective view of the sliding bearing device 100 in the assembled state, in which the impeller partly encloses the stand unit 105. FIG. 8 shows this sliding bearing device 100 as a section. The sliding bearing device 100 shown here is similar to the sliding bearing device described with reference to the preceding figures. According to the design example shown here, the impeller 110 comprises a plurality of flushing outlets 135. The discharge openings 140 of the flushing outlets are disposed at least partially in the transition section 510 between the propeller 515 and the jacket section 505. As an example, the discharge openings 140 are disposed evenly spaced around the periphery of the transition section 510. FIG. 7 shows a utilization of the flushing position of the plurality of flushing outlets having the suction force determined to be the strongest.

FIG. 8 shows a further sliding bearing device 100 for a cardiac support system. The figure shows a sectional view of a side view of the sliding bearing device 100. The stand unit 105 is partially enclosed by the jacket section 150 of the impeller 110. The plurality of discharge openings 140 of flushing outlets 135 is disposed in the transition region or transition section 510 between the propeller of the impeller 110 and the jacket section 150. The figure shows the flow direction of the pump fluid flow 115 and the flow path of the flushing fluid flow 130. The flushing fluid flow 130 is introduced through the flushing inlet 145 which, according to the design example shown here, is configured as a gap 905 between the base 107 of the stand unit 105 and the jacket section 505 of the impeller 110 enclosing the subsection 120 of the stand unit 105. The flushing fluid flow 130 is then conducted through the intermediate space 125 to one of the discharge openings 140 of the plurality of flushing outlets 135 by means of centrifugal force in order to flush the sliding bearing device 100.

Figure 9:
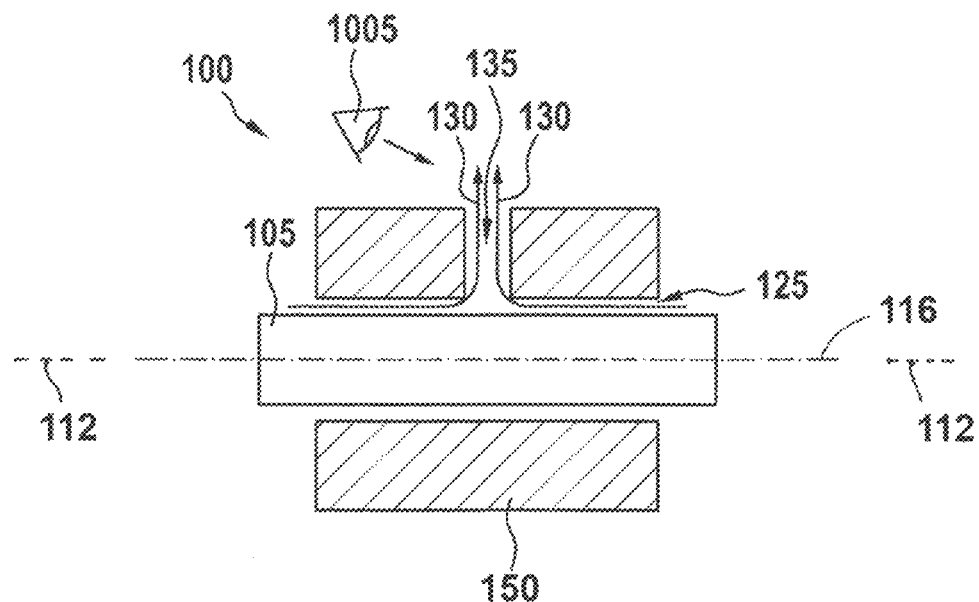
FIG. 9 a detail of a further sliding bearing device for a cardiac support system in a sectional view.

FIG. 9 shows a schematic illustration of a detail of a sliding bearing device 100 for a cardiac support system according to one design example. The figure shows a cross-section of a part of the sliding bearing device 100 with the subsection of the stand unit 105 enclosed by the jacket section 150 of the impeller. The configuration of the flushing outlet 135 here is intended to show that the flushing outlets can also be disposed in a non-mirror-symmetrical manner.

The figure shows a portion of the flushing path of the flushing fluid flow 130 that flows through the intermediate space 125 to the flushing outlet 135 and is discharged from the discharge opening of the flushing outlet 135. The outflow of the flushing fluid flow is shown in the following FIG. 10 with the aid of a plan view from the direction identified here with the arrow 1005.

Figure 10:
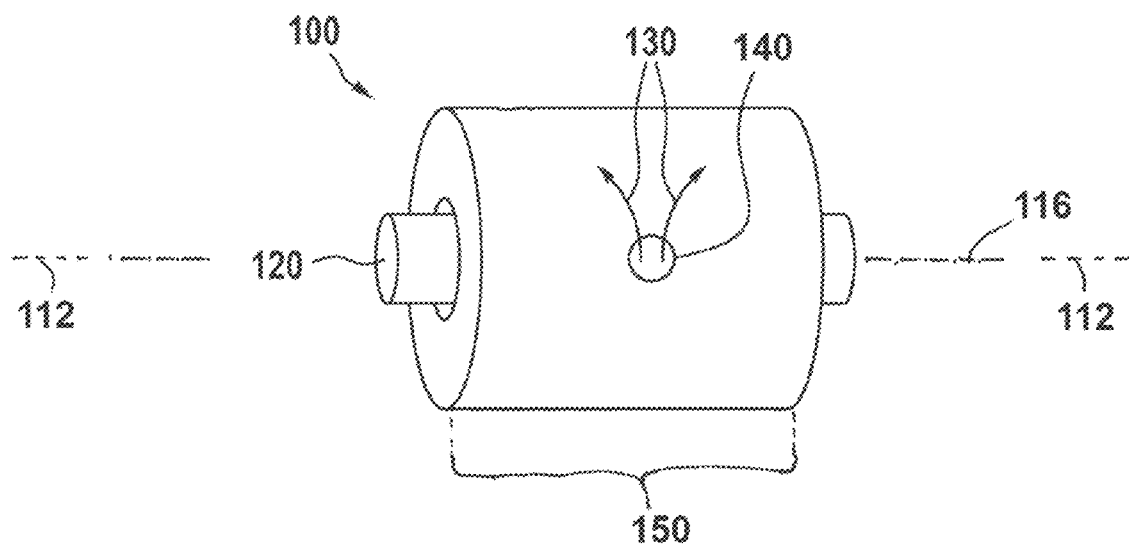
FIG. 10 the detail of the further sliding bearing device for a cardiac support system of FIG. 9 in a plan view.

FIG. 10 shows a schematic illustration of a detail of a sliding bearing device 100 for a cardiac support system according to one design example. The figure shows a plan view onto the detail of the sliding bearing device 100 identified in the preceding FIG. 9. The flushing outlet 135 is disposed in the jacket section 150 radially to a longitudinal extension axis 116 of the subsection of the stand unit 105 enclosed by the jacket section 505 which is aligned with the axis of rotation 112 in the bearing device. The flushing fluid flow 130 exits the jacket section 150 at the discharge opening 140 of the flushing outlet.

Figure 11:
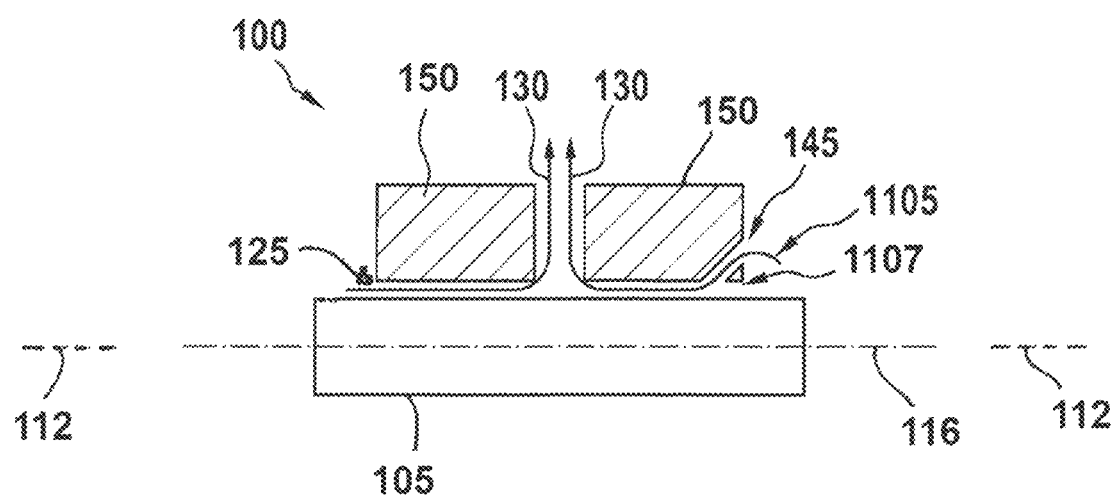
FIG. 11 a detail of a further sliding bearing device for a cardiac support system in a sectional view.

FIG. 11 shows a schematic illustration of a detail of a sliding bearing device 100 for a cardiac support system according to one design example. According to the design example shown here, the flushing inlet 145 is realized in the intermediate space 125 by a plurality of inlet channels, namely by the channel 1105 and the channel 1107. This is also intended to demonstrate that the inlet direction does not necessarily only have to be oriented in the direction of the longitudinal extension axis 116 of the bearing device 100 aligned with the axis of rotation 112 of the bearing device 100, but can also be inclined relative to said longitudinal extension axis. If the flushing inlet 145 is configured such that there is no acting centrifugal force there, for example such that the boundary of the flushing inlet 145 is not or only partially in the rotating body as in the design example of the flushing inlet 145 shown here as an inlet channel 1105 which is partially configured in the jacket section 150, the centrifugal pressure is advantageously increased.

Figure 12:
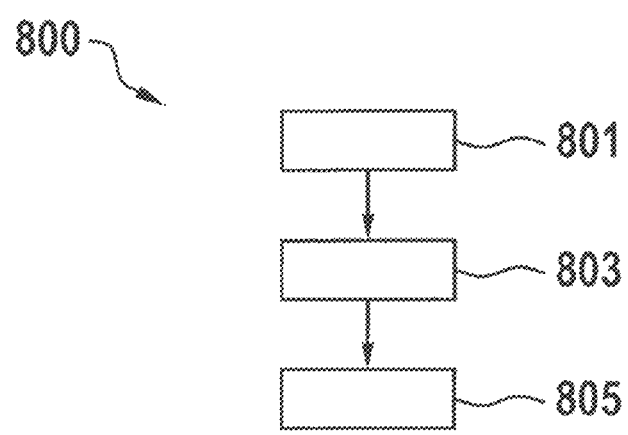
FIG. 12 a flow diagram of a method for producing a sliding bearing device.

FIG. 12 shows a flow diagram of a method 800 for producing a bearing device for a cardiac support system configured as a sliding bearing device or as a magnetic bearing device according to one design example. The method 800 comprises a step 801 of providing, a step 803 of forming, and a step 805 of assembling. In step 801 of providing, a stand unit is provided, which is configured to support an impeller such that it can rotate. Also provided in step 801 is the impeller, which is designed to rotate during an operation of the cardiac support system in order to convey a pump fluid flow. In step 803 of forming, at least one flushing outlet is formed in the impeller, which is designed to discharge a flushing fluid flow from the sliding bearing device by means of centrifugal force when the cardiac support system is in operation. In step 805 of assembling, the impeller and the stand unit are assembled to produce the sliding bearing device. At least one subsection of the stand unit is enclosed by the impeller. An intermediate space for guiding the flushing fluid flow is furthermore provided between said subsection and the impeller. During the operation of the cardiac support system, the flushing fluid flow is conducted from the intermediate space into the flushing outlet by means of centrifugal force and from there is discharged from the bearing device in order to flush the bearing device.

In summary, in particular the following should be noted: The invention relates to a bearing device 100 for a cardiac support system. The bearing device 100 comprises a stand unit 105 and an impeller 110. The stand unit 105 is designed to support the impeller 110 such that it can rotate. The impeller 110 is designed to rotate when the cardiac support system is in operation in order to convey a pump fluid flow 115. The impeller 110 is designed to enclose at least one subsection 120 of the stand unit 105 in the assembled state of the bearing device 100, wherein an intermediate space 125 for guiding a flushing fluid flow 130 is provided between the subsection 120 and the impeller 110. At least one flushing outlet 135 is formed in the impeller 110. The flushing outlet 135 is designed to discharge the flushing fluid flow 130 from the intermediate space 125 by means of centrifugal force when the cardiac support system is in operation.

The invention relates, in particular, to the aspects specified in the following clauses:

1. Sliding bearing device (100) for a cardiac support system (200), wherein the sliding bearing device (100) has the following features:
    a stand unit (105) is designed to support an impeller (110) such that it can rotate; and
    the impeller (110), which is configured to rotate when the cardiac support system (200) is in operation to convey a pump fluid flow (115), wherein the impeller (110) is designed to enclose at least one subsection (120) of the stand unit (105) in the assembled state of the sliding bearing device (100), wherein an intermediate space (125) for guiding a flushing fluid flow (130) is provided between the subsection (120) and the impeller (110), wherein at least one flushing outlet (135) is formed in the impeller (110), wherein the flushing outlet (135) is designed to discharge the flushing fluid flow (130) from the intermediate space (125) by means of centrifugal force when the cardiac support system (200) is in operation.
2. Sliding bearing device (100) according to clause 1, wherein a plurality of flushing outlets (135) are formed in the impeller (110).
3. Sliding bearing device (100) according to any one of the preceding clauses, wherein the at least one flushing outlet (135) is inclined relative to a longitudinal axis of the impeller (110).
4. Sliding bearing device (100) according to any one of the preceding clauses, wherein the flushing outlet (135) is configured as a tube having a discharge opening (140).
5. Sliding bearing device (100) according to clause 4, wherein the discharge opening (140) is disposed in a jacket section (505) of the impeller (110) enclosing the subsection (120) of the stand unit (105) or in a transition section (510) between a region of a propeller (515) of the impeller (110) and the jacket section (150).
6. Sliding bearing device (100) according to clause 5, wherein the impeller (110) comprises a plurality of flushing outlets (135), wherein the discharge openings (140) of the flushing outlets (135) are at least partially disposed in the transition section (510).
7. Sliding bearing device (100) according to any one of the preceding clauses, wherein a number of the flushing outlets (135) in the impeller (110) corresponds to a multiple of the number of blades of the impeller (110).
8. Sliding bearing device (100) according to any one of the preceding clauses, comprising a flushing inlet (145) for introducing the flushing fluid flow (130), wherein, in the assembled state of the sliding bearing device (100), the flushing inlet (145) opens into the intermediate space (125).
9. Sliding bearing device (100) according to clause 8, wherein the flushing inlet (145) is formed as a gap (905) between a base of the stand unit (105) and a jacket section (150) of the impeller (110) enclosing the subsection (120) of the stand unit (105), and/or wherein the flushing inlet (145) is formed in the impeller (110) as an inclined inlet channel (1105) or by a plurality of inlet channels having at least one inclined inlet channel (1105).
10. Sliding bearing device (100) according to any one of clauses 8 to 9, wherein the flushing inlet (145) is disposed downstream with respect to the flushing outlet (135) in the flow direction of the pump fluid flow (115).
11. Cardiac support system (200) comprising a sliding bearing device (100) according to any one of the preceding clauses 1 to 10.
12. Method (800) for producing a sliding bearing device (100) for a cardiac support system (200), wherein the method (800) comprises the following steps:
providing (801) a stand unit (105), which is designed to support an impeller (110) such that it can rotate, and the impeller (110), which is configured to rotate during operation of the cardiac support system (200) to convey a pump fluid flow (115);
forming (803) at least one flushing outlet (135) in the impeller (110), wherein the flushing outlet (135) is designed to discharge a flushing fluid flow (130) from the sliding bearing device (100) by means of centrifugal force when the cardiac support system (200) is in operation; and
assembling (805) the impeller (110) and the stand unit (105) to produce the sliding bearing device (100), wherein at least one subsection (120) of the stand unit (105) is enclosed by the impeller (110), and wherein an intermediate space (125) for guiding the flushing fluid flow (130) is disposed between the subsection (120) and the impeller (110).

LIST OF REFERENCE SIGNS

100 Sliding bearing device
105 Stand unit
107 Base
110 Impeller
111 Region of a propeller of the impeller
112 Axis of rotation
114 Longitudinal axis
115 Pump fluid flow
116 Longitudinal extension axis
120 Subsection of the stand unit
125 Intermediate space
130 Flushing fluid flow
132 Opening cross-section
134 Opening cross-section normal vector
135 Flushing outlet
136 Directional component
137 Axis
140 Discharge opening
145 Flushing inlet
150 Jacket section
155 Block
200 Cardiac support system
205 Housing section
210 Inlet hose
215 Discharge opening
220 Connection section
225 Web
405 Ball bearing
505 Jacket section
510 Transition section
515 Propeller
520, 525, 530 Region
605, 610, 615, 620, 625 Configuration
800 Method
801 Step of providing
803 Step of forming
805 Step of assembling
905 Gap
1005 Arrow
1105, 1107 Inlet channel

The invention claimed is:

1. A heart pump having a bearing device, the bearing device comprising:
a stand unit;
an impeller; and
an intermediate space formed between the impeller and the stand unit for conducting a flushing fluid flow from a fluid;
wherein the stand unit comprises a subsection enclosed by the impeller and configured to align the impeller about an axis of rotation,
wherein the impeller is configured to rotate about a longitudinal axis aligned with the axis of rotation when the heart pump is in operation to convey a pump fluid flow of the fluid in a flow direction,
wherein the impeller comprises at least one flushing outlet for discharging the flushing fluid flow from the intermediate space,
wherein the at least one flushing outlet comprises a first discharge opening for discharging the flushing fluid flow, which has an opening cross-section in which, an opening cross-section normal vector faces away from the axis of rotation and is radial to the axis of rotation,
wherein the impeller is disposed in a housing section comprising at least two second discharge openings for discharging the pump fluid flow and connected to an inlet hose for supplying the fluid, and
wherein the opening cross-section normal vector intersects with one of the at least two second discharge openings of the housing section at a time and is perpendicular to the axis of rotation.

2. The heart pump according to claim 1, wherein the at least one flushing outlet comprises a plurality of flushing outlets formed in the impeller.

3. The heart pump according to claim 1, wherein the at least one flushing outlet is tubular.

4. The heart pump according to claim 1, wherein the first discharge opening of the at least one flushing outlet is disposed in a jacket section of the impeller enclosing the subsection of the stand unit.

5. The heart pump according to claim 1, wherein the first discharge opening of the at least one flushing outlet is disposed in a transition section between a region of a propeller of the impeller and a jacket section of the impeller surrounding the subsection of the stand unit.

6. The heart pump according to claim 1, wherein the at least one flushing outlet comprises a plurality of flushing outlets formed in the impeller, the first discharge openings of the plurality of flushing outlets disposed at least partially in a transition section between a region of a propeller of the impeller and a jacket section of the impeller enclosing the subsection of the stand unit.

7. The heart pump according to claim 1, wherein a number of the flushing outlets formed in the impeller correspond to a multiple of a number of blades of the impeller.

8. The heart pump according to claim 1, wherein the housing section comprises webs, wherein the webs delimit the at least two second discharge openings for discharging the pump fluid flow.

9. The heart pump according to claim 1, wherein the bearing device is configured as a sliding bearing device comprising a sliding bearing for supporting a rotating component in the form of the impeller, or as a magnetic bearing device in which a rotating component in the form of the impeller is magnetically supported.

10. The heart pump according to claim 1, wherein a flushing inlet opens into the intermediate space in an assembled state of the bearing device.

11. The heart pump according to claim 10, wherein the flushing inlet is configured as a gap between a base of the stand unit and a jacket section of the impeller enclosing the subsection of the stand unit.

12. The heart pump according to claim 10, wherein the flushing inlet is configured as at least one inlet channel extending in a direction which intersects the longitudinal axis of the impeller or extends at an angle to the longitudinal axis of the impeller.

13. The heart pump according to claim 10, wherein the flushing inlet comprises a plurality of inlet channels.

14. The heart pump according to claim 10, wherein the flushing inlet is disposed downstream with respect to the at least one flushing outlet in the flow direction of the pump fluid flow.

15. The heart pump according to claim 1, wherein the impeller comprises a jacket section, the jacket section comprising an inner surface comprising a first constant radius from a longitudinal axis; wherein a flushing inlet is positioned at a first end of the jacket section and the at least one flushing outlet is positioned at a second end of the jacket section opposite the first end, wherein the intermediate space is parallel to the longitudinal axis between the flushing inlet and the at least one flushing outlet.

16. A method for flushing an intermediate space for guiding a flushing fluid flow with a fluid in a bearing device of a heart pump, the method comprising:
providing the intermediate space, the intermediate space comprising at least one flushing inlet for introducing the flushing fluid flow and at least one flushing outlet for discharging the flushing fluid flow, wherein the intermediate space is configured between an impeller which can rotate about an axis of rotation for conveying a pump fluid flow and a stand unit configured to align the impeller about the axis of rotation;
introducing the fluid into the intermediate space through the at least one flushing inlet;
expelling the fluid from the intermediate space through the at least one flushing outlet to at least one first discharge opening by means of a centrifugal force acting upon the fluid in the at least one flushing outlet relative to the axis of rotation, wherein the at least one flushing outlet comprises the at least one first discharge opening for an exit of the flushing fluid flow, wherein the at least one first discharge opening has an opening cross-section in which an opening cross-section normal vector faces away from the axis of rotation and is radial to the axis of rotation, wherein the impeller is disposed in a housing section connected to an inlet hose for supplying the fluid, wherein the housing section comprises at least two second discharge openings for discharging the pump fluid flow, and wherein the opening cross-section normal vector intersects with the at least two second discharge openings of the housing section and is perpendicular to the axis of rotation.

17. A heart pump configured to be delivered to the heart via catheter for pumping blood, the heart pump comprising:
a conduit having a discharge opening and configured to convey blood through the discharge opening into a blood vessel;
an impeller comprising a first magnet and configured to rotate about an axis to convey the blood; and
a support comprising a second magnet and configured to magnetically communicate with the first magnet to rotate the impeller, wherein the impeller and support define an intermediate space therebetween, the intermediate space configured to convey from a flushing inlet to a flushing outlet a portion of the blood conveyed through the conduit, the flushing inlet disposed downstream of the flushing outlet with respect to a direction of flow of the blood conveyed in the conduit, and the flushing outlet extending perpendicular to the axis;
wherein the flushing outlet extends in a direction that intersects the discharge opening of the conduit.

18. The heart pump according to claim 17, wherein the conduit comprises a tubular inlet hose connected to a tubular housing section.

19. The heart pump according to claim 17, wherein the flushing inlet defines a disc-like gap configured to receive blood from a plurality of angular locations about the axis.

20. The heart pump according to claim 17, further comprising a plurality of the flushing outlets defining elongated channels extending through the impeller.

* * * * *